(12) United States Patent
Campbell

(10) Patent No.: US 10,552,576 B2
(45) Date of Patent: Feb. 4, 2020

(54) SYSTEM AND METHOD FOR MACHINE BASED MEDICAL DIAGNOSTIC CODE IDENTIFICATION, ACCUMULATION, ANALYSIS AND AUTOMATIC CLAIM PROCESS ADJUDICATION

(76) Inventor: Stanley Victor Campbell, Vienna, VA (US)

( * ) Notice: Subject to any disclaimer, the term of this patent is extended or adjusted under 35 U.S.C. 154(b) by 0 days.

(21) Appl. No.: 13/281,349

(22) Filed: Oct. 25, 2011

(65) Prior Publication Data
US 2012/0166212 A1 Jun. 28, 2012

Related U.S. Application Data

(60) Provisional application No. 61/406,672, filed on Oct. 26, 2010.

(51) Int. Cl.
*G06F 19/00* (2018.01)

(52) U.S. Cl.
CPC .................. *G06F 19/328* (2013.01)

(58) Field of Classification Search
CPC .............. G06Q 50/22; G06Q 50/24
USPC .............................. 705/2, 3; 3/2, 3
See application file for complete search history.

(56) References Cited

U.S. PATENT DOCUMENTS

| | | | |
|---|---|---|---|
| 5,519,607 A | 5/1996 | Tawil et al. | |
| 6,988,088 B1 | 1/2006 | Miikkulainen et al. | |
| 7,213,009 B2 | 5/2007 | Pestotnik et al. | |
| 7,356,460 B1* | 4/2008 | Kennedy et al. | 704/9 |
| 7,433,828 B2 | 10/2008 | Brinkman et al. | |
| 7,801,740 B1 | 9/2010 | Lesser et al. | |
| 7,840,422 B1* | 11/2010 | Hail et al. | 705/4 |
| 7,873,525 B1 | 1/2011 | Kraus et al. | |
| 2001/0039503 A1 | 11/2001 | Chan et al. | |
| 2002/0091549 A1* | 7/2002 | Provost et al. | 705/4 |
| 2002/0107824 A1 | 8/2002 | Ahmed et al. | |
| 2003/0069760 A1 | 4/2003 | Gelber | |
| 2003/0083903 A1 | 5/2003 | Myers | |
| 2003/0149597 A1 | 8/2003 | Zaleski et al. | |
| 2004/0034549 A1 | 2/2004 | Winston et al. | |
| 2004/0078231 A1 | 4/2004 | Wilkes et al. | |
| 2004/0172297 A1* | 9/2004 | Rao et al. | 705/2 |
| 2005/0137910 A1 | 6/2005 | Rao et al. | |
| 2005/0234740 A1 | 10/2005 | Krishnan et al. | |
| 2005/0261941 A1 | 11/2005 | Scarlat et al. | |

(Continued)

OTHER PUBLICATIONS

International Search Report dated May 12, 2012.
Carl Sassenrath, "Context-dependent vs. Context-independent Computer Languages," Jan. 17, 2005, available at http://www.rebol.com/article/0104.html.

(Continued)

*Primary Examiner* — Linh Giang Le
(74) *Attorney, Agent, or Firm* — Miles & Stockbridge P.C.

(57) ABSTRACT

A context sensitive methodology, a Structured Virtual Construct (SVC) system, data tagging techniques, and an apparatus are provided for performing Medical Code-based decision-making involving the matching of a given medical identified element against one or more of a set of known or reference medical identified elements from history or other data elements. A satisfactory decision is achieved as a function of both aggregated ranking (AR) and account adjudication (AA), where account adjudication refers to the full set of values garnered by the Medical Code accumulation process in the process of generating approval/denial/reclassification/of medical diagnosis and/or claim events.

12 Claims, 1 Drawing Sheet

(56) References Cited

U.S. PATENT DOCUMENTS

| | | | |
|---|---|---|---|
| 2006/0047539 A1* | 3/2006 | Huang | 705/4 |
| 2006/0149603 A1* | 7/2006 | Patterson et al. | 705/4 |
| 2006/0200010 A1 | 9/2006 | Rosales et al. | |
| 2007/0033158 A1* | 2/2007 | Gopalan | G01J 1/58 |
| 2007/0106536 A1 | 5/2007 | Moore et al. | |
| 2008/0040151 A1 | 2/2008 | Moore et al. | |
| 2008/0208912 A1* | 8/2008 | Garibaldi | G06Q 10/06 |
| 2008/0214928 A1 | 9/2008 | Rosales et al. | |
| 2008/0319796 A1 | 12/2008 | Stivoric et al. | |
| 2009/0062623 A1 | 3/2009 | Cohen et al. | |
| 2009/0099862 A1* | 4/2009 | Fireman | G06F 19/3418 705/2 |
| 2009/0210251 A1 | 8/2009 | Callas | |
| 2009/0210253 A1 | 8/2009 | Ash et al. | |
| 2009/0299767 A1 | 12/2009 | Michon et al. | |
| 2010/0023346 A1 | 1/2010 | Paty et al. | |
| 2010/0049625 A1 | 2/2010 | Biebesheimer et al. | |
| 2010/0100396 A1 | 4/2010 | Daven et al. | |
| 2010/0161316 A1* | 6/2010 | Haug | 704/9 |
| 2010/0191691 A1 | 7/2010 | Hudson et al. | |
| 2010/0235197 A1 | 9/2010 | Dang et al. | |
| 2011/0112848 A1 | 5/2011 | Beraja et al. | |
| 2011/0196704 A1 | 8/2011 | Mansour et al. | |
| 2011/0201905 A1 | 8/2011 | Spencer et al. | |
| 2011/0225114 A1 | 9/2011 | Gotthardt et al. | |

OTHER PUBLICATIONS

Cynthia Dwork et al., "Rank aggregation revisited," Manuscript, 2001, available at http://citeseerx.ist.psu.edu/viewdoc/summary?doi=10.1.1.23.5118.

Macdonald and Ounis, "Learning models for ranking aggregates," Proceedings of the European Conference on IR Research, Berlin, Heidelberg, pp. 517-529, 2011, available at http://citeseerx.ist.psu.edu/viewdoc/summary?doi=10.1.1.186.7604.

D. Sculley, "Rank aggregation for similar items," In SDM, 2007, available at http://citeseerx.ist.psu.edu/viewdoc/summary?doi=10.1.1.152.5939.

Supplemental European Search Report of EP 11 83 6967 dated June 22, 2015.

European Office Action issued in Patent Application No. 11 836 967, dated May 24, 2016.

Australian Office Action issued in Patent Application No. 2011319965, dated Apr. 14, 2016.

George D. Magoulas et al., "Machine Learning in Medical Applications", Advanced Course on Artificial Intelligence '99, Springer-Verlag Berlin Heidelberg, 2001.

Jennifer Boger et al., "A Planning System Based on Markov Decision Processes to Guide People with Dementia Through Activities of Daily Living", IEEE Transactions on Information Technology in Biomedicine 10.2 (2006).

* cited by examiner

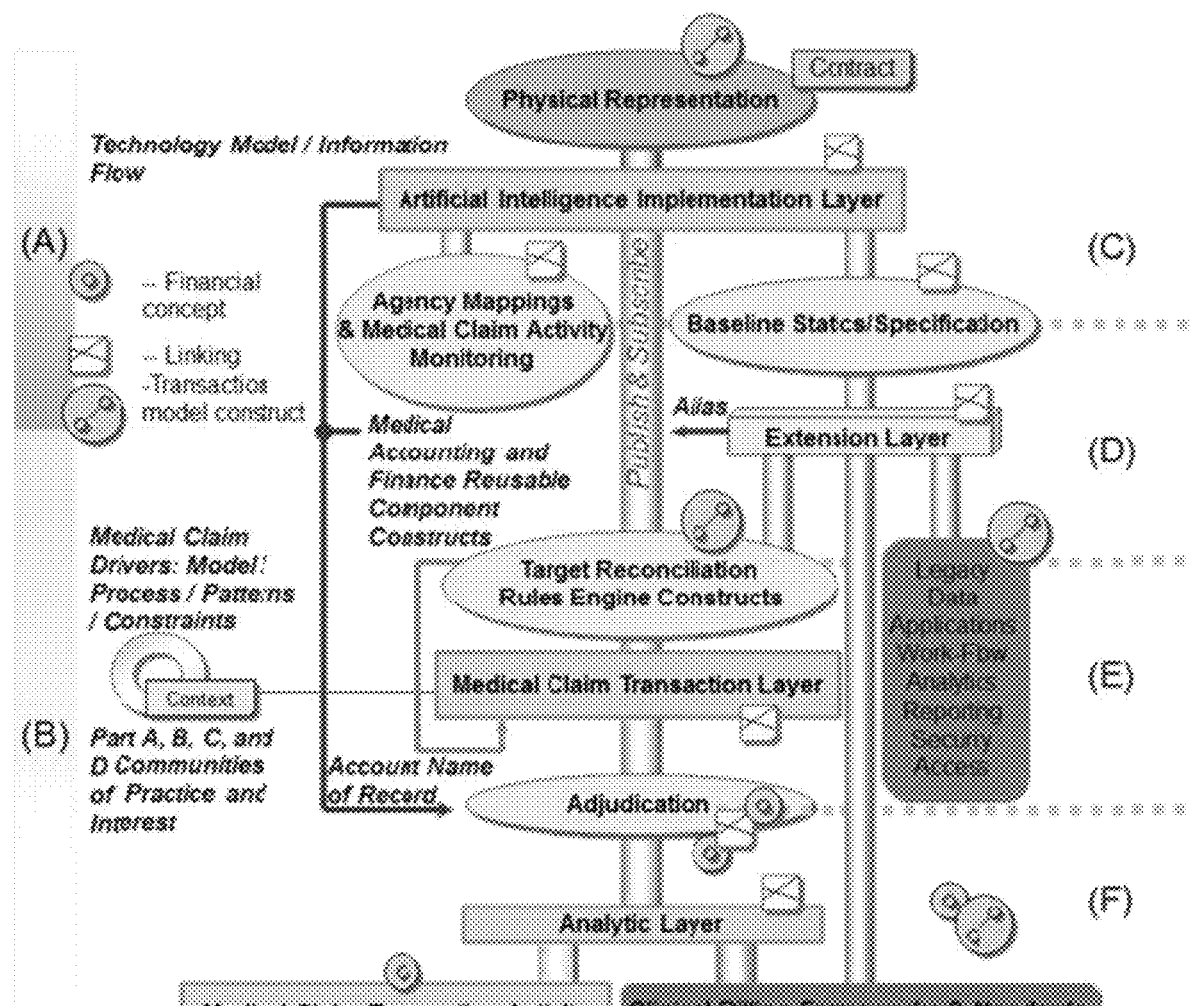

SYSTEM AND METHOD FOR MACHINE BASED MEDICAL DIAGNOSTIC CODE IDENTIFICATION, ACCUMULATION, ANALYSIS AND AUTOMATIC CLAIM PROCESS ADJUDICATION

CROSS-REFERENCE TO RELATED PATENT APPLICATIONS

This application claims priority to U.S. Provisional Patent Application No. 61/406,672, filed Oct. 26, 2010, which is incorporated herein by reference in its entirety.

BACKGROUND OF THE INVENTION

Field of the Invention

Methodologies, systems, and apparatuses for performing Medical Code-based decision-making related to matching a given medical identified element against one or more of a set of known or reference medical identified elements is disclosed herein.

Brief Description of Related Art

Fraudulent and erroneous medical claims are a serious problem, causing an estimated tens of billions of dollars in annual losses to insurance companies and governmental agencies.

The current system of medical claims processing, management, payment and reconciliation involves multiple stages of manual processes and workflows which are augmented by automated accounting and documentation systems. However, individual insurance companies maintain a vast number of clinicians and disparate automated systems which are prone to varying degrees of limitations inherent to human dependent systems run buy independent companies. The deficiencies within the current systems has created an industry of commercial insurance and government Recovery Audit Contractors (RAC's), whose payments are based on similar human review by clinicians and legal experts whose ultimate benefit is the sharing of recovered payment.

Given this fact and the natural incentive for RAC's to focus on high cost claims, there remains a significant number of un-recouped improper payments made, which now exceeds $24 billion per year for CMS claims alone as based on the Office of Management and Budget (OMB) estimates.

SUMMARY OF THE INVENTION

A rule-based method utilizing neural computational logic, statistically motivated algorithms and a computationally efficient artificial intelligence management approach to non-linear dimensionality reduction of options that has form, fit, and functionality preserving properties and connection to clustering for representation of high-dimensional data for performing Medical Code-based decision-making is disclosed, wherein said method comprises generating a set of Medical Code Options based on preliminary information regarding an initial assertion, and applying a rule set to each Medical Code option to generate a result of: (1) accumulate and aggregate further information to apply to a Medical Code option, (2) render an automatic reclassification of a medical code option, (3) generate an auto-accept decision for a medical code option, and (4) generate auto-deny.

Various systems for performing the same are also disclosed. It is to be understood that both the foregoing general description and the following detailed description are exemplary and explanatory only, and are not restrictive of the invention as claimed.

BRIEF DESCRIPTION OF THE DRAWINGS

FIG. 1 is a block architecture diagram of a system for performing Medical Code-based decision-making according to one aspect of the presently disclosed methods, systems, and apparatuses.

The symbol  indicates that a computation involves a financial concept. The symbol  indicates that a computation involves a transaction model construct. The symbol  indicates linkage of one or more computations. The area of the FIGURE represented by Bar (A) indicates transactions involving Medical Claim Activity Monitoring. The area of the FIGURE represented by Bar (B) indicates transactions involving Application and analytic processing. The section indicated by (C) indicates Transaction / Presentation layers, including Finance and Accounting Specifics, such as Mandatory versus Optional; financial elements versus attributes; Automated versus manual data-entry and masking, workflow routing and packaging, and service parameters. The section indicated by (D) indicates Authorization and Security layers, including Role-Process Identification; Standards & Framework Adoption; Qualifier to Object Breakout; Thesaurus Assignment; and Transaction Interchange Mapping. The section indicated by (E) indicates Technology Requirements layers, including Medical Claim Rules / Patterns; Atomics & Alerts; Structure: Resolution / Adjudication; Workflow / Process identification; Mandatory versus Optional; and Sub-set Application Layer. The section indicated by (F) indicates Semantics and Logic layers, including Medical Claim, Temporal, Spatial Context; Use Case and Work-Flow Sequence; Authoritative Sources; Medical Claim Activity and Reporting; Concepts Registration; Classification/Categorization Assignment; and Ontology/Taxonomy Placement.

DETAILED DESCRIPTION OF THE INVENTION

This presently disclosed methods, systems, and apparatuses employ an Artificial Intelligence based apparitions managed within a Neural Network of varying automated elements, which automatically review each medical claim and billing for the purpose of replacing human processes related to expert medical analysis, authorization, rejection, or re-classification (re-price) billings which do not meet the existing guidelines for payment. These methods, systems, and apparatuses are further designed to develop and report metrics which classify improper payments on claims for services that do not meet Medicare's medical necessity criteria; for services that are incorrectly coded; for claims that should have been paid by a different health insurance company or Medicare Secondary Payer (MSP); for claims related to outdated fee schedules; and for claims made twice (or more) because duplicate (multiple) claims were submitted. The designed ingest of historical data and the analysis of the report metrics are used to employ a system of machine based automated continuous self learning.

In an aspect, a methodology, a system, and an apparatus for performing Medical Code-based decision-making related to matching a given medical identified element against one or more of a set of known or reference medical identified elements is disclosed herein. A satisfactory decision is achieved as a function of both aggregated ranking and account adjudication, where account adjudication, although technically describing just one element in the approval value set, refers to the full set of values garnered by the Medical Code accumulation process in the process of generating approval/denial/re-classification/medical claim events. Aggregated ranking is a mechanism to set the various "correlation adjudication values," where the thresholds may be set within the system to define acceptable adjudication parameters for decision-making. The Medical Code is computed on the basis of partial matching of feature vector elements, where separate and distinct feature vectors are associated with both the given medical identified element and each of the reference medical identified elements. Feature vector element values are used to support the Rules Engine and assist in the decision-making process. Following Medical Code-combination methods (e.g., those used in Least Squares Fit for linear analysis, Monte Carlo computational sampling, Markov chain discrete steps and Dempster-Shafer formalisms), the Medical Code is accrued for both the approval and denial decisions regarding a potential match.

In an aspect, the methodologies, systems, and apparatuses disclosed herein apply statically based analysis in conjunction with the specific application of algorithms relating plausibility and potentiality of accuracy to form the system baselines and the dynamic update of those baselines for determining whether a given medical code is accurate.

In another aspect, a context sensitive methodology, a Structured Virtual Construct (SVC) system, data tagging techniques, and an apparatus are provided for performing Medical Code-based decision-making involving the matching of a given medical identified element against one or more of a set of known or reference medical identified elements from history or other data elements is disclosed. A satisfactory decision may be achieved as a function of both aggregated ranking (AR) and account adjudication (AA), where account adjudication refers to the full set of values garnered by the Medical Code accumulation process in the process of generating approval/denial/re-classification/ of medical diagnosis and/or claim events. Aggregated ranking is a mechanism to set the various correlation adjudication values, where the thresholds define acceptable adjudication parameters for decision-making Medical Code aggregated ranking is computed on the basis of partial matching of feature vector elements, where separate and distinct feature vectors are associated with both the given medical identified element and each of the reference medical identified elements. Following Medical Code-combination methods, diagnosis, or symptom descriptivism, Medical Codes are accrued for both the approval and denial decisions regarding a potential match. Subsequent Medical Code event (MCE) profiles are used to track medical outcomes and trends. Human Feedback may further be employed to enhance automated system learning.

The presently disclosed methods, systems, and apparatuses are useful, for example, in decision-making situations where it is preferable to generate a large number of Medical Code Options, and authorize, reclassify and/or deny these Medical Code Options dynamically.

As used herein, the phrases "reclassify", "auto-reclassify", "auto-reclassification", and "automatically reclassify" shall all refer to a command to change a target medical code to a different, more appropriate code.

As used herein, the phrase "authorize", "accept", "auto-accept", and "automatically accept" shall refer to a command to accept a given medical code as probably valid to a degree of confidence as defined by the rule set.

As used herein, the phrase "auto-deny" shall refer to a command to deny a given medical code as probably invalid to a degree of confidence as defined by the rule set.

The presently disclosed methods, systems, and apparatuses are also useful for those cases where it is important to minimize false denials. Historically a large number of initial "false approvals" are tolerated (followed by subsequent more detailed analysis and determinations for cost recovery), with many "false approvals" at risk cost thresholds being allowed to avoid adjudication. Examples of such cases include the daily execution and adjudication of doctors, hospitals, Medicare or Medicaid claims processing, medical profile screening for complex surgery, etc.

Similarly, the presently disclosed methods, systems, and apparatuses are useful when a large number of possible determinations or associations can be made regarding an medical identified element, e.g., determining which Provider, Patient, or reference medical identified element is referred to when a provider's name, a person's name, or an extracted medical identified element is taken from some Medical Record, claims document or other data source. Here, there is again a need to post many possible alternative matches; e.g., initially to all reference medical identified elements which have matching or even similar names, nomenclature, or components. A portion of the objectives are to advance multiple candidate Medical Code Options across each coding discipline (Durable Medical Equipment (DME), Medicare Parts A-D, Hospice, etc.) and to approve or deny each, until a very small number (preferably a single Medical Service code) remains as the most appropriate match given full consideration to governance and regulation.

The process of approving (validating), reclassifying (refuting and re-calculating) or denying (refuting) any number of Medical Code Options is impacted by several factors. This is not a linear classification task. In a classification task, the number of particular classes is typically well-known, and typically much smaller than the number of candidate medical identified elements that would be matched to a given class type. Because classes can be described by combinations of "characteristic attributes," classification tasks can typically be performed by one of a number of well-known methods, e.g., statistical classifiers, neural networks, etc. However, the presently disclosed methods, systems, and apparatuses address the case of matching particulars—e.g., a given extracted medical identified element (e.g., a person's name and medical event code) against a large set of reference medical identified elements (for example, ICD-9 or CPT codes) and/or individual patient history (e.g., historical Common Working File (CWF) of known persons and medical history). In this case, each reference medical identified element is characterized uniquely by a set of particulars, not as a member of a given class. This means that a methodology other than that typically employed for classification tasks will be required.

As used herein, the phrase "medical code" shall refer to any system used to document a medical event and/or to bill that medical event to an insurance company, government payer, or other institution or person compiling information regarding the medical event. By way of example and not limitation, the World Health Organization publishes The International Statistical Classification of Diseases and Related Health Problems (most commonly known by the abbreviation ICD), which is a medical classification that provides codes to classify diseases and a wide variety of signs, symptoms, abnormal findings, complaints, social circumstances, and external causes of injury or disease. Under this system, every health condition can be assigned to a unique category and given a code up to six characters long. The ICD system is is used by most insurance companies and government agencies worldwide. In the typical case, a level of medical service, once determined by qualified staff, is translated into a standardized five digit procedure code drawn from the Current Procedural Terminology (CPT) code set which maintained by the American Medical Association through the CPT Editorial Panel database. The verbal diagnosis is translated into a numerical code set forth by the ICD. These two codes, a CPT and an ICD-9-CM (will be replaced by ICD-10-CM as of Oct. 1, 2013) are equally important for claims processing.

As used herein, the phrase "medical identified element" shall refer to any information associated with a given medical event.

As used herein, the phrase "medical code identified element" shall refer to any information associated with a medical code in a given medical claim, including but not limited to a medical code, a symptom, a diagnosis, an indication, a test result, or any other information used to support the assignment of the medical code to the medical claim.

As used herein, the phrase "Provider identified element" shall refer to an identified element associated with a given medical care provider. By way of example and not limitation, this includes Medicare enrollment information for providers, physicians, non-physician practitioners, and other suppliers. CMS has established standards for information and maintains that information within its Provider Enrollment, Chain and Ownership System (PECOS) as an alternative to the paper (CMS-855) enrollment process. PECOS is designed to allow physicians, non-physician practitioners and provider and supplier organizations to enroll, make a change in their Medicare enrollment, view their Medicare enrollment information on file with Medicare, or check on status of a Medicare enrollment application. In an aspect, the provider identified elements are selected from elements required by PECOS, which may be augmented with other legal information and association elements not required for maintenance by the government. By way of example and not limitation, the provider identified elements may be obtained from information compiled from PECOS.

As used herein, the phrase "Patient identified element" shall refer to an identified element associated with a given patient. By way of example and not limitation, the patient identified element may include: demographic information including, but not limited to, the patient's name, address, social security number, home telephone number, work telephone number and their insurance policy identity number; guarantor information of a parent or an adult related to the patient; military status, such as whether the patient is a veteran active duty military, or reservist; racial or ethnic information; a summary of treatment, including but not limited to one or more diagnoses, and/or the reason for the visit, the nature of the illness, examination details, medication lists, diagnoses, and suggested treatment.

As used herein, the phrases "reference identified element" shall refer to an identified element in a set of identified elements associated with historical medical claims, against which an extracted medical identified element may be compared to determine a probability of whether the extracted identified element is properly associated with the medical code and/or claim. The reference identified elements may be drawn from a knowledge base of compiled identified elements associated with various Codes/Claims, or may be generated dynamically from one or more external data sources.

As used herein, the phrase "Rules Set" shall refer to a pre-programmed set of rules applicable to content or appliances, to follow for determining whether a given medical identified element supports or refutes a proposition that a given medical claim should be approved, disapproved, or reclassified. By way of example and not limitation, guidelines for approving or denying claims based on ICD codes are well known in the art and publically available. Such rules are generally applied by clinicians and medical claims experts and may be applied in the presently described methods, systems, and apparatuses.

In an aspect, a set of extracted medical identified elements, extracted provider identified elements, and extracted patient identified elements associated may be compared to a set of reference medical identified elements associated with the same or similar codes using an appropriate rule set, until a sufficient confidence can be reached regarding whether an acceptable code decision can be made to accept, reject, or automatically reclassify a given claim. In a further aspect, the process proceeds iteratively, with each extracted medical identified element being compared against the set of reference medical identified elements to generate a confidence level regarding the correctness or incorrectness of a given decision until a confidence threshold for an acceptable code decision has been reached.

In a further aspect, all the thresholds for making an acceptable decision are context-dependent. Frequently, there will be costs associated with reaching certain levels of adjudication parameter or approval in a given decision. Depending on the quality of available data, the number of competing Medical Code Options, the extent to which these Medical Code Options can be readily distinguished from each other based on the readily available data, and other factors, it may at times be more "costly" to achieve greater adjudication parameters in either or both validating and/or refuting any of the set of potential Medical Code Options. It may at times be possible to deny certain critical Medical Code Options more readily than it may be possible to authorize, reclassify a approval assertion. In all of these cases, the question of setting thresholds for an acceptable decision becomes paramount, as cost factors can rise rapidly as decision adjudication parameter requirements are increased. Thus, it is useful to have a means for making context-dependent thresholds for "acceptable decisions." In this manner, review by clinicians, administrators and legal review is replaced by the described methods, reducing overall review time from days and weeks to nano-seconds.

The Medical Service approval/deny methods may comprise at least a Medical Code accumulation method or system for incrementally aggregating information until a satisfactory decision can be reached, where this method should yield both degrees of approval and denial for any given Medical Service, as well as to indicate when an aggregated Medical Code combination can authorize, reclassify or deny a given Medical Service, or map " Rules Conflict" related the specific Medical Service.

An ability to deal with partially complete and/or partially erroneous Medical Code, as part of the Medical Code accumulation method, both associated with the extracted medical identified element and also with the reference medical identified elements to which the extracted medical identified element will be compared for Medical Service resolution.

A Medical Code selection method or system for selecting the "reclassification" type of Medical Code to both access and aggregate in order to form the next step of aggregated Medical Code that serves to either authorize, reclassify or deny a Medical Service, where the means for such selection needs to address both the potential "maximal usefulness" that a given piece of Medical Code could provide as well as its potential cost, together with the likelihood that even if acquired, it could possibly be erroneous or incomplete.

As one example, the presently disclosed methods, systems, and apparatuses address the case where a medical identified element (person, organization, place, object, medical code event, etc) is extracted from text-based data sources. There are already many methods and capabilities for performing this task, and for purposes of the presently disclosed methods, systems, and apparatuses, they will be assumed to provide an acceptable set of extracted identified elements which may further already be identified, using one or more of several means known to practitioners of the art, as being a person, place, thing, etc. Further, without loss of generality, the presently disclosed methods, systems, and apparatuses may be independent of the data source from which the identified elements are extracted; the sourcing data may be structured or unstructured. In the case of structured data, there is often a set of feature vector elements associated with the identified element; e.g., in the case of a list of persons, there can also be associated information such as address and phone number. In the case of unstructured data, it is also often possible to create a "context vector" containing both words and other extracted medical identified elements which can be useful for identifying a given extracted medical identified element in the context of either or both a situation or reference frame as well as other specific extracted medical identified elements.

The presently disclosed methods, systems, and apparatuses defines an acceptable methodology for accumulating Medical Code with regard to decision-making corresponding to a particular assertion, e.g., medical identified element matching. The challenges which one aspect of the present presently disclosed methods, systems, and apparatuses addresses are those decision-making situations where it is substantially preferable to generate a large number of Medical Code Options, and both "authorize, reclassify" and "deny" these Medical Code Options, until a final decision can be made. The presently disclosed methods, systems, and apparatuses are particularly useful for those cases where it is exceptionally important to minimize "false denials." Indeed, in many circumstances, a large number of initial "false approvals" can be tolerated (followed by subsequent more detailed analysis and determinations), rather than allow any "false denials" to escape. Examples of such cases include security screening for passengers on an aircraft, medical profile screening such as cancer cell/tumor detection, etc.

The presently disclosed methods, systems, and apparatuses address the challenges previously identified with a decision-making methodology, architecture, and system that includes at least three components of presently disclosed methods, systems, and apparatuses: (1) a system for generating multiple candidate Medical Code Options, each of which are to be authorize, reclassify and/or deny, until minimally few Medical Code Options remain as viable candidates, (2) a system for determining context-based Medical Code accumulation thresholds corresponding to "acceptable decisions" regarding candidate Medical Code Options, along with (3) a system for Medical Code selection and aggregation, in support of the Medical Code Options approval and deny tasks.

The means for generating candidate Medical Code Options is largely governed by the particular situation to which the decision-making method, architecture, and system will be applied.

The goal of Medical Service approval is typically to provide sufficient Medical Code to approve or make a given assertion. One application of the disclosed methodologies, systems, and apparatuses thus is to determine a correct association between an "extracted medical identified element" and one out of a set of "reference medical identified elements." This process will typically continue until an approval match has been made.

Illustrative, although by no means limiting, examples include the following: A person solicits and receives Medical Services for a kidney transplant procedure and the medical providers (doctors, nurses, hospital, staff etc.) gives certain identifying information itemizing each element (the "extracted medical identified elements") for billing purposes. Though each individual element may be properly identified, coded and priced, the governance protocol for the insurance company or government payer may have a fixed or negotiated price for the complete procedure. The presently disclosed methods, systems, and apparatuses are designed to sufficiently match the itemized elements to the operable referenced medical identified element beginning with the proper identification of the individual and their benefits and ending with the full review of each procedure code.

Once a Provider or Patient has been associated to some known reference medical identified element (e.g., using as an example the Center for Medicare and Medicaid's CWF file or one or more commercial data sources), the same person must be confirmed as not likely being on a "Fraud or un-approved vender/patient list?" To this end, a Medical Service deny function is provided to minimize the number of false denials resulting from making a given assertion, e.g., with regard to extracted medical identified element evaluation. Such a function may use list matching may be used. For example, the person or vendor may be screened against: (i) known Fraud List persons, and/or (ii) their potential for "non-obvious relationships", for example, multiple drug transactions from disparate Providers to the same person, multiple drug transactions from a single Provider to the same person over and above an authorizable dosage and/or multiple drug transactions from a single Provider to the same person, processed by multiple disparate vendors. As such, the system, methods, and apparatuses may be configured to refuting a match between an extracted medical identified element and a key reference medical identified element, which is useful in determining the significance of material associated with the extracted medical identified element.

The case of Medical Service deny (e.g., of List matching to known and trusted sources) may use advancing match Medical Code Options to multiple candidates drawn from some reference list of persons (from, for example, agency or company eligibility registry, Dun and Bradstreet, Lexus Nexus, etc. or government and commercial issued Fraud List or "access denied" list). Such a method is useful to advance a large number of candidate Medical Code Options, thereby generating a very large pool of potential "approval candidates," and then to deny these matches.

The decision-making processes here are typically of two interwoven types. Both the tasks of Medical Service approval and Medical Service deny require a Medical Code-aggregation and evaluation methodology and system. This methodology and system should produce sufficient Medical Code that matches to known reference content with some degree of fidelity.

The difference between Medical Service approval and Medical Service deny is that the goal of Medical Service approval is to garner sufficient Medical Code to support a given (medical identified element-verifying) match. The process should involve not only gathering evidential support, but also (i) ensuring that there are no substantive denials in the proposed verification, and (ii) there are no significant conflicts introduced by matches to other Medical Code, Provider, or Patient referenced in the data sources. The process of Medical Service Code denial similarly garners sufficient Medical Code to support denial in a match, preferably with minimal approval and conflict.

Thus, the presently disclosed methods, systems, and apparatuses define a method, architecture, and system by which context-dependent critical decision thresholds can be achieved, i.e., formulating a means by which critical decision thresholds can be modified as a set of one or more external events or parameters, thus yielding context-dependent decision criteria, as a function of both account adjudication and aggregated ranking, which are defined herein.

In order to fulfill the related goals of Medical Service approval and deny, Medical Code needs to be gathered and aggregated in support of each candidate Medical Service.

The approach taken in the presently disclosed methods, systems, and apparatuses addresses those cases where various "medical identified elements" can be described by means of feature vectors, where the feature vectors can take on population of additional, pre-specified data fields as need for additional Medical Code arises. Note that not all fields are filled at the beginning of the decision-making task, nor must all the fields necessarily be filled in order for a satisfactory decision to be reached. Additionally, the decision process is influenced through a Feedback Loop via human adjudication of reconciled Code/Claims.

The tasks to which this methodology will be applied will involve the following constraints: The a priori probability distribution of the feature vector values may be unknown, and a priori dependence of the extracted medical identified element association to a reference medically allowable identified element, resting on a given set of feature vector values, may be difficult to compute, and the number of possible competing Medical Code Options, and the effort needed to distinguish an acceptable match to a specific Medical Service (verifying one Medical Service and refuting others), can be very difficult to specify in advance.

Further, the following objectives may be satisfied such as Medical Code accumulation should be traceable, different kinds of Medical Code can be associated with both the extracted medical identified elements and the reference medical identified elements, so that no single "path" for Medical Code matching will always be required to be available. In circumstances where multiple Medical Code combinations may not only be possible but necessary, Medical Code items (feature vector elements) associated with either or both the extracted medical identified elements and/or the reference medical identified elements may be partial or incomplete, and yet partial matches between these Medical Code items should contribute some degree of Medical Code accumulation, both re-classification and conflict in potential decisions/assignments should be represented explicitly, there should be a defined means for accumulating additional Medical Code to support potential assertions, so that a "minimal-cost" set of rules for obtaining Medical Code can be applied (assuming that each "Medical Code unit" carries an associated cost), and there should be a means to cut-off further Medical Code accrual after the sufficient Medical Code has been obtained to support a given assertion, while the re-classification and/or conflict about this assertion are within acceptable and defined limits.

The presently disclosed methods, systems, and apparatuses postulate a rule-based decision-making method for generating Medical Code Options based on preliminary information that can be ascertained either with regard to the initial assertion(s), and then gathering sufficient Medical Code to deny the majority of the Medical Code Options, while simultaneously approving, reclassifying or "validating" the Medical Service that is most correct.

As used herein, the phrase "rules based decision making" shall refer to the application of statics, algorithms, temporal and geospatial associations, and rules in rendering an appropriate code decision.

In the typical case, once the a medical procedure and diagnosis codes for a given claim are determined, the medical provider will document the decision and the biller will transmit the claim to the insurance company (payer). This is usually done electronically by formatting the claim as an ANSI 837 file and using Electronic Data Interchange to submit the claim file to the payer directly or via a clearinghouse. Historically, claims were submitted using a paper form; in the case of professional (non-hospital) services and for most payers the CMS-1500 form or HCFA (Health Care Financing Administration claim form) was commonly used. The CMS-1500 form is so named for its originator, the Centers for Medicare and Medicaid Services. Currently approximately 30% of medical claims get sent to payers using paper forms which are either manually entered or entered using automated recognition or OCR software. Within two years all providers will be required to have automated submission. In the present methods, systems, and apparatuses, statically based analysis is used in conjunction with the specific application of algorithms relating to plausibility and potentiality of accuracy to form the system baselines and the dynamic update of those baselines. The proximity of time and place also may play a part in the system adjustments. The rules based decision uses functions of the baselines to administer the understanding and action of the system.

In an aspect, a Dempster-Shafer algorithm is used. By way of example, a Structured Virtual Construct Dempster-Shafer (SVC-DS) may be used. The SVC-DS process produces a approval-set output for each iteration of the SVC-DS process (each successive step of pairwise Medical Code aggregation). This approval-set consists of the various initial and resultant Medical Code valuations (approval, denial, and re-classification, along with account adjudication). In addition, a conflict value can be produced after two or more Medical Code items are combined. This measures the disparity between the approvals that one Medical Code source might assert against the denial asserted by a different form of Medical Code. Thus, instead of having a scalar adjudication parameter value we have not less than a set of three distinct values (approval, denial, and re-classification), along with two others that are additive combinations of certain distinct values.

The goal of using the SVC-DS method is to provide support for a decision. That decision should rightly be made in the context of several different factors and with regard to the medical identified element in question, potential classifications or matches of the medical identified element, and considerations of both potential past as well as future history. In short, the decision-making process that the SVC-DS method supports is not static, rather decisions related to the Feedback Loop is made in context. It is to this end that the first aspect of the presently disclosed methods, systems, and apparatuses are specifically addressed.

The process of refuting Medical Code Options requires that a measure of denial be generated as well as approval in the leading Medical Code Options. Also, the leading Medical Code Options should mature into ones where there is minimal conflict; i.e., no strong indicators of both approval and denial Further, when there are multiple competing Medical Code Options, and multiple small "Medical Code items" being used to form Medical Code "masses" in support of various Medical Code Options, and where there is also high likelihood of partial, incomplete, and even erroneous "Medical Code items" that will be found and used, there will be a great deal of ambiguity in the early processing stages. Thus, it is very reasonable to work with measures of re-classification, supporting both account adjudication and Medical Reasoning, as much as to work with the more certain statements regarding approval and denial. For these reasons, a Dempster-Shafer formalism alone is not always an appropriate starting place for grounding the methods discussed in the presently disclosed methods, systems, and apparatuses.

In an aspect, the SVC model framework is applied to the managing Dempster-Shafer formalism stimulus information for node responses by: (1) using a tractable statics and algorithm management for computing the modeled estimate of the most probable stimulus to have generated an observed single or multiple trained or modeled response, given a prior distribution model over the medical reasoning stimulus; (2) using a gaussian approximation to the medical reasoning feature vector distribution that can be used to quantify the fidelity with which various stimulus features are encoded; (3) using a method for estimating the mutual information between the medical reasoning feature vector distribution and spike trains emitted by a neural cluster; and (4) using a framework for the detection of medical reasoning feature vector distribution change events or times (the time at which the medical reasoning feature vector distribution undergoes a change in mean or variance) by establishing limits and boundaries over the medical reasoning feature vector distribution.

This combination of support elements makes the SVC-Dempster-Shafer method suitable for Medical Code aggregation within the overall decision-support architecture. The use of the Least Squares Fit method along with the SVC-DS allows for linear rules based organization and ranking of explicit pairwise combination of approvals, along with measures of re-classification and denial in a given assertion.

A challenge in using a method such as SVC-DS in conjunction with the Least Squares Fit is that the initial approval-set values are readily defined in an "a priori" sense as are the normal distributions used in associated cluster based classifications. Much like work with neural networks, which can be trained when there are sufficient examples "spanning" the multiple dimensions for Medical Code combinations, it is reasonably assured of complete Medical Code-space coverage required for good training. Therefore, means for defining not only initial approval, but also denial and re-classification resulting from any initial Medical Code form may be applied, prior to the Medical Code aggregation.

Because one of the strengths of the SVC-DS method is that it is intrinsically well-suited for dealing with aggregation of partial or incomplete Medical Code, a method is employed that not only defines the relative initial values of each specific type of Medical Code, and also the value of "partial" Medical Code of each type, but also the means by which denial is associated with a given Medical Code-type when approval falls off. This may be determined prior to aggregating a particular Medical Code type with other (either initial and singular, or previously aggregated) Medical Code. The present the presently disclosed methods, systems, and apparatuses described herein address this issue.

While the need for a decision tree governing selection of pairwise elements for combination can require development of a substantial rules set to cover all the possible cases for obtaining different Medical Code combinations, this is actually proven to be an advantage in the sense that each time a Medical Code-unit is requested from a specific source, it is possible to pre-compute the additional cost. It is also possible to specify in advance how much a given additional form of Medical Code will be allowed to contribute to the total approval ranking This means that cost/benefit tradeoffs for collecting different forms of Medical Code from different sources can be assessed, leading to a rules set governing Medical Code-gathering.

Aggregated ranking can also be used to address benefit, as an indirect function of risk. In this case, the "risk" is associated with the expense of making a focused effort to reach a particular subgroup of Providers, Patients, or Payees. In the cases of focused Provider Enrollment and Management, or collecting of improperly paid debts, it is important to assess the exceptional benefit that could result from investing greater attention or effort to adjudicate the individual claim billing for hospitals, physicians, skilled nursing facilities, labs, ambulance companies, and durable medical equipment (DME) suppliers. All configurations are designed to maintain rules and adjudication processes which have associated nuances of billing which are processed individually.

Account adjudication, as used in this approach defines the parameters and certainty that a given assertion is true related to the approval. Additionally the degree to which it is credible that a given assertion could come from Trusted Knowledge Base information is directly proportional to degree of accuracy in the account adjudication for approval re-classification, and denial. The presence of a re-classification measure makes it possible to express both account adjudication and doubt. It is also a way to express what is not known about a given Provider, Patient, of Medical Coding situation. This makes it possible to identify and account for Medical Code conflicts; as an example, when one Medical Code element supports the approval that a claim is authorized and other Medical Code says that the event should have been bundled and is no longer approved for Medical Services. When conflicts increase, the need to gather/assess more Medical Code for verification increases.

According to one aspect of the presently disclosed methods, systems, and apparatuses, the account adjudication concept can be used multiple ways in the approach to medical identified element verification. For example, in medical identified element medically allowable identified element verification the use establishes that an medical identified element is correctly identified in terms of known information that can be associated with that medical identified element.

In the case of medical identified element matching, high confidence means that it is directly associative that a given medical identified element matches to some specific known, reference medical identified element. The difference between this case and the previous is that in the first, the reference medical identified element is actually the one being posited for medically allowable identified element verification, and the verification information can come from multiple disparate sources, which may collectively confirm different attributes associated with the medical identified element. The process focuses on accumulating sufficient adjudication parameter in confirming information provided by potentially disparate sources against the information provided about the medical identified element whose medically allowable identified element is being verified. In contrast, medical identified element matching assumes that the medical identified elements who could be matched (the reference medical identified elements) are largely already known, and that sufficient already-vetted information is attached to each of these so that the task is more one of matching the given extracted medical identified element (the one being matched) against one of these reference medical identified elements through the use and extension of dedicated rules. There would preferably be some attributes or context associated with the extracted medical identified element, and there would preferably be a larger set of attributes associated with each reference medical identified element. Preferably, also, the attributes and/or context associated with the extracted medical identified element form a subset of the attributes and/or context associated with the reference medical identified element, to facilitate the matching process.

In an aspect, a rule-based method for performing Medical Code-based decision-making on a computer-based system comprising at least one processor is provided, wherein said at least one processor: (a) generates a set of Medical Code Options based on preliminary information regarding an initial assertion data, and (b) applies a rule set to each Medical Code option to generate a result selected from the group consisting of: (b1)) accumulate and aggregate further information to apply to a Medical Code option, (b2) render an automatic reclassification of a medical code option, (b3) generate an auto-accept decision for a medical code option, and (b4) generate auto-deny. A Structured Virtual Construct (SVC) Dempster-Shafer (SVC-DS) output where the estimate of "Plausibility and Potentiality" proves to be a good measure of limitation and control of trained data in variety of model formats, including the ability to tractably perform optimal nonlinear feature vector reconstruction given the activity of ensembles of interacting rules models or some similarly focus function is essential and may be applied to each medical code option to generate the result.

In an aspect, the initial assertion is related to the method of utilizing neural computational logic, statistically motivated algorithms and a computationally efficient artificial intelligence management approach to nonlinear dimensionality reduction of options that has form, fit, and functionality preserving properties and connection to clustering for representation of high-dimensional In one aspect, a system for performing Medical Code-based decision-making comprising at least one processor is provided, wherein said at least one processor is programmed to perform a set of functions comprising: (a) a Medical Code processor function configured to match at least one class of extracted medical identified elements against a set of reference medical identified elements (RMIE); (b) a Medical Provider Code processor function configured to match an extracted medical identified element associated with Provider identification against a set of reference medical Provider identified elements (RMPrIE); (c) a Medical Patient Code processor function configured to match an extracted medical identified element associated with the Patient Name of Record against a set of reference medical Patient identified elements (RMPaIE); (d) a Medical Code selection processor function configured to define and apply a rule set to the extracted medical identified element and a large indefinite quantity (LIQ) of reference medical identified elements to generate a total Medical Code identification function; (e) a Medical Code threshold processor function configured to generate a context-dependent threshold for an acceptable code decision; and (f) a decision processor function configured to compare the total Medical Code function to the context-dependent threshold to generate a result selected from the group consisting of: (f1) accumulate and aggregate further Medical Code aggregation, (f2) render an automatic reclassification, (f3) generate an auto-accept decision, and (f4) generate auto-deny.

As used herein, the phrase "large indefinite quantity" shall refer to any quantity of information generated dynamically from at least one data source, such that the quantity of information is sufficient to raise the level of confidence regarding a given decision. In an aspect, the "large indefinite quantity" may be derived from the total number of claims processed by the a large insurance company, the Department of Defense, the Veterans Administration and/or CMS for a given time period. In a further aspect, the large indefinite quantity is continuously adjusted until the confidence is raised above the threshold level.

The set of reference medical identified elements in each of the foregoing systems may be obtained from a Knowledge Base that is stored on computer readable medium, or may be generated dynamically through reference to databases or other sources. Moreover, each of the RMIE, RMPrIE, and RMPaIE are maintained in the same Knowledge Base or separately along with NIH maintained Medical and Pharmaceutical terms and definitions, CPT and ICD-9 coding. In an aspect, the system comprises a Knowledge Base comprising RMIE, a Knowledge Base comprising RMPrIE, and/or a Knowledge Base comprising RMPaIE.

The processor may be further programmed to perform a Medical Code event processor function to generate medical code event profiles to track medical outcomes and trends. Medical Code event processing inherently produces access to several other important and useful quantities of information including approved diagnosis, treatment plans and prescription drugs each of which may be quantified in a probability structure to which uncertainty is inherent. Simple alerts can be made to both providers and patients for follow-up (calendar alert for follow-up, e-mail alert for prescription renewal, etc), however history files and real time patient tracking allows the system to perturb or monitor patient tracking against established baselines with the potential of adjustments being made slightly in some direction for some small positive or negative scalar made as a result of computing the ratio of anticipated posterior results at two points (start point and current point extrapolated to current point and forecasted end point or equivalently the difference in the log posterior (forecasted end point). If the posterior in process end points are managed virtually within the system changes significantly with the diagnosis, then this change is easily "detectable", "forecastable" and highly discriminateable from the prescription or the baseline. Conversely, if the size of the in process posterior points are small and it is difficult to discriminate between statistical baseline and proscribed medical coding. On the basis of the data one could expect the estimate to be highly variable in this direction and a corresponding confidence interval as established by a Dempster-Shafer algorithm could serve to limit the significant number of needless follow-up visits or extended patient stay. In affect, sick people are treated quicker and well people are identified earlier.

The system may further comprise a user interface configured to permit human feedback to enhance automated system learning. In some circumstances, Human feedback related to medical claims analysis and processes by experienced clinicians, billing, accounting and legal experts may be desired for various uses of the analytic functionality described. Additionally, human feedback from patents related to self-monitoring can be used to enhance the baseline of the individual beyond that of the generalized norm established by the history file. In the example of a patient who has had Congestive Heart failure, remote monitoring or self reporting could include online monitoring or reporting of: a) Blood pressure, Pulse, Weight, and Diet through home devices and automated logbook of monitored results. Here, human feedback will enhance automated learning while empowering the potential of automated alerts from machine learning.

The processor may be further programmed to accumulate and aggregate a set of enhanced reference medical identified elements against which each of the extracted medical identified element will be matched. As used herein, the term "enhanced reference medical identified elements" refers to a reference medical identified element which has been cross-tested against an outside data source. For example, in the case where the reference medical identified element is maintained in a Knowledge Base, a second independent data source may be accessed to provide supplemental data regarding the reference medical identified element to generate a new set of medical identified elements against which the extracted medical identified element may be tested. By way of example and not limitation, the second independent data source may be a claims made to the Veteran's Administration or through CMS.

The system may further comprise one or more data sources configured to enhancements of the medical identified elements in the form of either feature vector elements and/or corrections to feature vector elements for either of the reference medical Provider, Patient, or Code identified elements and the extracted medical diagnostic identified elements, thereby generating a large indefinite quantity of augmented feature vectors for each of the large indefinite quantities of extracted medical identified elements and/or the reference medical identified elements. These enhancements may range from a simple correction in a patient or provider address to the complete addition of the ICD-10 code. The data sources may be any computer-accessible source comprising data relevant to the extracted medical identified elements. Exemplary data sources include, but are not limited to, data compiled and maintained by the Veteran's Administration, CMS and other authorized sources. In an aspect, the one or more data sources may be stored on a computer-readable medium, and/or configured to provide data for: (1) a set of reference Provider identified elements, Patient identified elements, and medical identified elements, and (2) a set of enhanced reference medical identified elements configured to augment a large indefinite quantity of feature vectors associated with each of the large indefinite quantity of extracted medical identified elements, thereby generating a large indefinite quantity of augmented feature vectors for each of the large indefinite quantity of extracted medical identified elements.

In most cases it is likely that any assertion posed by the rules configuration formalism will need to withstand queries regarding its believability. Bayesian methods may be used in this area. Alternatively, the Dempster-Shafer (SVC-DS) method may also be used.

The Medical Code selection processor function may further comprise: a Medical Service generator function configured to generate one or more Medical Code Options about the extracted or referenced medical identified element; and a Medical Service approval processor function configured to authorize, reclassify, and/or deny the generated Medical Code Options to generate a total Medical Code function, wherein the total Medical Code function is computed uniquely and distinctively for each Medical Service regarding a potential match between Provider, Patient, an extracted medical identified element and a reference medical identified element.

The Medical code selection processor function may be further configured to apply a rule set to generate a large indefinite quantity of Medical Code Options and to gather data to authorize, reclassify or deny the generated Medical Code Options.

A threshold processor function is involved in all measurable analytic functions and may be further configured to define the context-dependent threshold for an acceptable code decision by applying an auditable rule set using an aggregated ranking calculation and account adjudication calculation.

The processor may be further programmed to perform: (g) a reconciliation processor function configured to: (g1) acquire additional Medical Code information from the one or more data sources, according to the rule set provided by the Medical Code selection processor function, for the extracted medical identified element and each of its associated linear and non-linear matches to a reference medical identified element or enhanced reference medical identified element; (g2) evaluate the linear and non-linear matches and determine if additional Medical Code is required to evaluate the linear and non-linear matches; and (h) a second Medical Code processor function by which the additional Medical Code is aggregated with the existing Medical Code associated with the extracted medical identified element, forming an expanded feature vector set uniquely associated with the extracted medical identified elements.

The Medical Code processor function may be further configured to accumulate Medical Code tracking so that the Medical Codes are traceable. In an aspect, disparate metadata from various functional elements within the system and/or from data sources are used to create metadata silos across the system enterprise. This function allows the consolidated view of vital metadata relationships comprised in the decision process of an acceptance, rejection or reclassification to be preserved. This function of Medical Code Tracking provides an ability to perform impact analysis and to provide the data lineage needed to justify the system assessment for data usage, end-to-end impact analysis, and report-to-source data lineage. In an aspect, the function is designed to serve as a central management tracker. This function also serves as the integration point to various external content management solutions such as Microsoft Windows, Tomcat, UNIX (Linux, Solaris, and IBM AIX), IBM WebSphere, Weblogic from Oracle BEA, and Oracle Application Server (OAS).

The extracted medical identified elements and reference medical identified elements may be configured to comprise a large indefinite quantity of feature vectors. In an aspect, the feature vectors of the reference medical identified elements are fully populated with a large indefinite quantity of element values and if element values are unfilled, probability value is placed on an adjudication threshold relative to the degree and criticality of the non-populated element. In another aspect, at least one of the large indefinite quantity of feature vectors comprises a large indefinite quantity of vector elements. In another aspect, the Medical Code processor may be configured to obtain additional element values for the large indefinite quantity of reference medical identified element feature vectors.

In another aspect, a system for performing Medical Code-based decision-making from a set of data elements is provided, the system comprising: (a) a large indefinite quantity of extracted medical identified elements stored on a computer readable medium, wherein each extracted medical identified element has associated with it a large indefinite quantity of feature vectors each having a large indefinite quantity of feature vector elements; (b) a set of reference medical identified elements stored on a computer readable medium; (c) a set of enhanced reference medical identified elements stored on a computer readable medium; (d) one or more data sources stored on a computer readable medium, configured to enhancements in the form of either feature vector elements and/or corrections to feature vector elements for either or both the reference medical identified elements and the extracted medical identified elements, thereby generating a large indefinite quantity of augmented feature vectors for each of the large indefinite quantity of extracted medical identified elements and/or the reference medical identified elements; (e) at least one processor programmed to perform: (e1) a Medical Code processor function configured to compare the large indefinite quantity of augmented feature vectors associated with each of the large indefinite quantity of extracted medical identified elements against a large indefinite quantity of feature vectors for the set of reference medical identified elements or the set of enhanced reference medical identified elements; and (e2) a threshold processor function configured to generate a context-dependent threshold for an acceptable decision.

The processor may be further programmed to perform a Medical Code selection processor function configured to define a large indefinite quantity of rule sets to be applied to each of the large indefinite quantity of extracted medical identified elements and the large indefinite quantity of reference medical identified elements and configured to generate an initial set of extracted medical identified elements.

The rule sets may be derived by performing a multidimensional lookup task and characterizing the large indefinite quantity of vector elements of the large indefinite quantity of feature vectors against normative values. The rules modeling multidimensional lookup serves as a analytic and reporting function used to model, analyze, test and save business rules as executable decision services. The system supports all aspects of the modeling process, from initial capture of Medical Code processing requirements through the testing of the decision against organizational data—delivering complete, payment ready decision services. The advanced multidimensional analysis function for decision logic validation of comprehensive medical claims scenario-based models also include template-based reporting for documentation and audit. Business Rules Metrics and Reporting is also used to manage all run-time aspects of decision services.

The processor may be further programmed to perform a reconciliation processor function, configured to acquire an additional Medical Code from the one or more data sources, according to the rule set provided by the Medical Code selection processor function, for each member of the candidate approval pool of allowable claims and each of its associated linear and non-linear matches to a reference medical identified element or enhanced reference medical identified element.

The processor may be further programmed to perform a second Medical Code processor function by which the additional Medical Code is aggregated with an existing Medical Code associated with a candidate approval medical identified element, forming an expanded feature vector set uniquely associated with the candidate approval medical identified element. This function is designed to mimic the clinicians methods of consolidating individual codes into a single consolidated code.

The processor may be further programmed to perform a decision processor function, configured to apply an evaluation to the new feature vector associated with a given candidate approval medical identified element, to further refine the previous decision as to whether the candidate approval is a definite match, a definite not-match, or requires more Medical Code identification or analysis for Medical Service adjudication or deny regarding its linear or non-linear match against a enhanced reference medical identified element or a reference medical identified element.

The Medical Code selection processor function may further comprises a Medical Service generator function configured to generate one or more Medical Code Options about each of the large indefinite quantity of extracted medical identified elements; and a Medical Service approval processor function configured to authorize, reclassify, and/or deny the generated Medical Code Options to generate the initial set of extracted medical identified elements. In an aspect, the Medical Code Options generator function may be configured to apply the rule set to generate a large indefinite quantity of Medical Code Options, and the Medical Code processor function may be configured to apply the rule set to gather data to authorize, reclassify or deny the generated Medical Code Options.

The threshold processor function may further be configured to apply the rule set to define the context-dependent threshold for an acceptable decision using an aggregated ranking calculation and account adjudication calculation.

The set of enhanced reference medical identified elements comprises various permutations of the referenced medical identified elements, wherein the set of enhanced reference medical identified elements is larger than and inclusive of the set of reference medical identified elements. In an aspect, the reference medical identified elements and the enhanced reference medical identified elements are related as different versions of a medical code system, for example ICD 9 (reference medical identified elements) and ICD 10 (enhanced reference medical identified elements).

In another aspect, a system for performing Medical Code-based decision-making is provided, the system comprising at least one processor programmed to perform: (a) a Medical Code processor function, configured to compare a large indefinite quantity of augmented feature vectors associated with each of a large indefinite quantity of extracted medical identified elements against a large indefinite quantity of feature vectors for a set of reference medical identified elements or a set of enhanced reference medical identified elements; and (b) a threshold processor function, configured to generate a context-dependent threshold for an acceptable decision.

The system may further comprise one or more data sources configured as enhancements of the medical identified elements in the form of either feature vector elements and/or corrections to feature vector elements for either of the reference medical Provider, Patient, or Code identified elements and the extracted medical diagnostic identified elements, thereby generating a large indefinite quantity of augmented feature vectors for each of the large indefinite quantities of extracted medical identified elements and/or the reference medical identified elements. The data sources may be any computer-accessible source comprising data relevant to the extracted medical identified elements such as those anticipated by the inclusion of ICD-10 coding. Exemplary data sources include, but are not limited to, data sources maintained by the Veterans Administration and CMS. In an aspect, the one or more data sources may be stored on a computer-readable medium, and/or configured to provide data for: (1) a set of reference Provider identified elements, Patient identified elements, and medical identified elements, and (2) a set of enhanced reference medical identified elements configured to augment a large indefinite quantity of feature vectors associated with each of the large indefinite quantity of extracted medical identified elements, thereby generating a large indefinite quantity of augmented feature vectors for each of the large indefinite quantity of extracted medical identified elements.

A dynamic representation of Medical Coding and Claims Rules may further be provided, where different nodes are activated to a degree to which there is Medical Code supporting their approval as a true state of affairs, to serve as a means by which Medical Code is accrued to support approval. In some cases, an assertion posed by the rules configuration formalism will need to withstand scrutiny regarding its believability. Bayesian methods may be applied. Alternatively, the Dempster-Shafer (SVC-DS) method may be employed, in which both measures of approval as well as denial. This method uses the combination of both to serve as a more powerful means for handling Medical Code in support (as well as against) an assertion.

The processor may be programmed to perform a Medical Code selection processor function for defining a rule set to be applied to the extracted medical identified element and the large indefinite quantity of reference medical identified elements and configured to generate an initial set of extracted medical identified elements.

The processor may be programmed to perform a reconciliation processor function, configured to acquire additional Medical Code from the one or more data sources, according to the rule set provided by the Medical Code selection processor function, for each member of the initial set of extracted medical identified elements and each of its associated linear and non-linear matches to a reference medical identified element or enhanced reference medical identified element;

The processor may programmed to perform a second Medical Code processor function, by which an additional Medical Code is aggregated with an existing Medical Code associated with the extracted medical identified element, forming an expanded feature vector set uniquely associated with that extracted medical identified element.

The processor may programmed to perform a decision processor function, configured to apply an evaluation to a new feature vector associated with the extracted medical identified element, to further refine a previous decision as to whether the candidate approval is a definite match, a definite not-match, or requires more Medical Code for Medical Service deny regarding its linear or non-linear match against a enhanced reference medical identified element or a reference medical identified element.

The Medical Code selection processor function may be further configured to generate an initial set of extracted medical identified elements by: (1) a Medical Service generator function configured generate one or more Medical Code Options about the extracted medical identified element; (2) a Medical Provider approval processor function configured to authorize, reclassify or deny a Medical Provider Option generated by the Medical Service generator function; (3) a Medical Patient approval processor configured to authorize, reclassify, and/or deny a Patient Medical Code Option generated by the Medical Service generator function; and (4) a Medical Service approval processor function configured to authorize, reclassify, and/or deny a Medical Code Option generated by the Medical Service generator function.

The rule set may used by the Medical Code Options generator function to generate a large indefinite quantity of Medical Code Options and by the Medical Code processor function to gather data to authorize, reclassify, or deny the Medical Code Options generated by the Medical Service generator function. In an aspect, the rule set is derived by performing a multidimensional lookup task and characterizing the large indefinite quantity of vector elements of the large indefinite quantity of feature vectors against normative values. In a further aspect, a primary information vector, an activity vector and a context vector is provided for each extracted medical identified element. The primary information vector refers to at least one item of personally identifying information associated with an extracted medical identified element, such as, for example, a Patient name; a relationship or potential relationship to another Patient; or a date of birth. The activity vector may comprise at least one item of information associated with a treatment course in the extracted medical identified element, such as, for example, treatment history, prescription history and profile information and/or Provider statement information. The context vector may comprise structured, unstructured, or semi-structured contextual information related to the information contained in the activity vector, such as the date, time, and place.

In another aspect, a system for performing automated security screening using Provider, Patient and Medical Code-based decision-making is provided, the system comprising at least one processor programmed to perform: (a) a Medical Code processor function, configured to match an extracted medical identified element against a set of reference medical identified elements; (b) a Medical Code selection processor function, configured to (b1) define a rule set to be applied to the extracted medical identified element and the large indefinite quantity of reference medical identified elements and (b2) generate a total Medical Code function; (c) a threshold processor function configured to generate a context-dependent threshold for an acceptable decision; and (d) a decision processor function, configured to compare the total Medical Code function to the context-dependent threshold and determine whether to accumulate and aggregate further Medical Code or to generate a decision.

In a further aspect, a primary information vector, an activity vector and a context vector is provided for each extracted medical identified element. The primary information vector refers to at least one item of personally identifying information associated with an extracted medical identified element, such as, for example, a Patient name; a relationship or potential relationship to another Patient; or a date of birth. The activity vector may comprise at least one item of information associated with a treatment course in the extracted medical identified element, such as, for example, treatment history, prescription history and profile information and/or Provider statement information. The context vector may comprise structured, unstructured, or semi-structured contextual information related to the information contained in the activity vector, such as the date, time, and place.

In another aspect, a system for performing Medical Code-based decision-making is provided, the system comprising a processor configured to: (a) match an extracted medical identified element against a set of reference medical identified elements; (b) match an extracted Provider identified elements against a set of reference Provider identified elements; (c) match an extracted Patient identified elements against a set of reference medical Patient identified elements; (d) define a rule set to be applied to the extracted medical identified element and the large indefinite quantity of reference medical identified elements and configured to generate a total Medical Code function; (e) generate a context-dependent threshold for an acceptable decision, wherein the context-dependent threshold is a function of an aggregated ranking value and account adjudication value; and (f) compare the total Medical Code function to the context-dependent threshold and determine whether to accumulate and aggregate further Medical Code or to generate a decision-result.

The aggregated ranking value may be independent of any information about the extracted medical identified element and is a measure representative of a need to obtain more information about the extracted medical identified element.

The account adjudication value may be a degree to which it is auditable.

The aggregated ranking value may be independent of any information about the extracted medical Provider identified element and is a measure representative of a need to obtain more information about the extracted medical Provider identified element.

The Patient account adjudication value is a degree to which the claim result of acceptance, denial or reclassification is auditable and that a given assertion can be traced.

As will be well understood by a person of ordinary skill in the art, each of the identified functions in the foregoing systems may be performed by a single processor or a plurality of processors. Additionally, a single processor may be programmed to perform a single identified function or a plurality of functions.

EXAMPLES

FIG. 1 is a flow chart of an exemplary method, system, and apparatus as disclose herein.

The approach is designed to extend the capabilities of Medical Claims adjudication and review well beyond the existing functionality with best of breed technology. The system is designed to control data movement and migration with a novel ability to write it to various targets. Alternatively, as we transition to a dynamic data transfer from established MEDICAL CLIENT legacy data, the system can access and convert this content through ODBC drivers. This Medical Claim Transition Activity serves as the first step in the Artificial Intelligence navigation. Here the Clinical Billing Framework serves as the graphical user interface from which we define and manage data maps for relational and non-relational data sources as we target optional personal metadata profiles and perform database row tests. By performing a row test on a data map, we can view the source data formatted into our Data Dictionary for conversion into objects. (For CMS this includes Imbedded Variable Length record fields). The MEDICAL CLIENT Data Dictionary system component manages data maps for non-relational files and tables and maintains them in the DATAMAPS file. This portion of the system handles bulk data extraction requests from the Analytic Layer for preparation for Adjudication. If the MEDICAL CLIENT data source or target is on a system that is remote from the one on which we are using, we will extract bulk data from and load bulk data to the following types of databases and files: Relational databases and flat files on Linux, UNIX, and Windows; DB2 tables and flat files on i5/OS; Relational databases, non-relational databases, and sequential data sets on MVS; Microsoft SQL Server; Oracle; and Sybase tables on Linux, UNIX, or Windows.

The invention claimed is:

1. A computer-based Artificial Intelligence (AI) method for performing Medical Code-based decision making comprising:
   analyzing, by an AI based computer utilizing neural computational logic, medical and contextually related data, using AI in an iterative context sensitive methodology for performing Medical Code-based decision-making comprising a matching of a given medical identified element against one or more of a set of known or reference medical identified elements, wherein the AI comprises one or more of a least squares fit for linear analysis, a Monte Carlo computational sampling, a Markov chain discrete step and a Dempster-Shafer formalism; and
   determining, by an AI based computer, an acceptable code decision comprising a plurality of iterative decisions including matching the given medical identified element with the one or more of a set of known or reference medical identified elements to optimize a confidence level of correctness until a non-optimal confidence threshold for an acceptable code decision is reached.

2. The computer-based AI method of claim 1, wherein the Medical Code-based decision-making further comprises an aggregated ranking to determine a correlation adjudication value.

3. The computer-based AI method of claim 2, wherein the aggregated ranking generates a threshold that defines an acceptable adjudication parameter for decision-making.

4. The computer-based AI method of claim 1, wherein the acceptable code decision comprises rendering an automatic reclassification, executing an auto-accept decision or executing an auto-deny.

5. The computer-based AI method of claim 1, wherein the context sensitive methodology comprises determining a critical decision threshold that is modified based on a set of one or more external events or parameters.

6. The computer-based AI method of claim 1, wherein the AI further comprises a user interface configured to permit human feedback to enhance automated system learning.

7. A non-transitory computer readable medium with instructions stored thereon to perform Medical Code-based decision making, the decision making comprising:
   analyzing, by an Artificial Intelligence (AI) based computer utilizing neural computational logic, medical and contextually related data, using AI in a iterative context sensitive methodology for performing Medical Code-based decision-making comprising a matching of a given medical identified element against one or more of a set of known or reference medical identified elements, wherein the AI comprises one or more of a least squares fit for linear analysis, a Monte Carlo computational sampling, a Markov chain discrete step and a Dempster-Shafer formalism; and
   determining, by an AI based computer, an acceptable code decision comprising a plurality of iterative decisions including matching the given medical identified element with the one or more of a set of known or reference medical identified elements to optimize a confidence level of correctness until a non-optimal confidence threshold for an acceptable code decision is reached.

8. The non-transitory computer readable medium of claim 7, wherein the Medical Code-based decision-making further comprises an aggregated ranking to determine a correlation adjudication value.

9. The non-transitory computer readable medium of claim 8, wherein the aggregated ranking generates a threshold that defines an acceptable adjudication parameter for decision-making.

10. The non-transitory computer readable medium of claim 7, wherein the acceptable code decision comprises rendering an automatic reclassification, executing an auto-accept decision or executing an auto-deny.

11. The non-transitory computer readable medium of claim 7, wherein the context sensitive methodology comprises determining a critical decision threshold that is modified based on a set of one or more external events or parameters.

12. The non-transitory computer readable medium of claim 7, wherein the AI further comprises a user interface configured to permit human feedback to enhance automated system learning.

* * * * *